United States Patent [19]
Eckardt

[11] Patent Number: 6,074,882
[45] Date of Patent: Jun. 13, 2000

[54] DEVICE DETERMINING A CONCENTRATION OF A GAS MIXTURE

[75] Inventor: Bernd Eckardt, Bruchkoebel, Germany

[73] Assignee: Siemens Aktiengesellschaft, Munich, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/736,372

[22] Filed: Oct. 24, 1996

Related U.S. Application Data

[63] Continuation-in-part of application No. 08/367,707, filed as application No. PCT/DE93/00531, Jun. 21, 1993, abandoned.

[30] Foreign Application Priority Data

Jul. 2, 1992 [DE] Germany .......................... 42 21 692.3

[51] Int. Cl.[7] .................................................. G01N 25/22
[52] U.S. Cl. ........................ 436/147; 73/25.01; 422/83; 422/94; 422/95; 422/96; 422/97; 422/98; 436/144; 436/155; 376/300; 376/301; 376/313; 423/580.1; 423/580.2
[58] Field of Search ............................. 73/25.01; 422/83, 422/94, 95, 96, 97, 98; 436/144, 147, 155; 376/300, 301, 313; 423/580.1, 580.2

[56] References Cited

U.S. PATENT DOCUMENTS

| | | | |
|---|---|---|---|
| 1,957,341 | 5/1934 | Holt | 23/255 |
| 3,399,398 | 8/1968 | Beckek et al. | 340/237 |
| 4,072,043 | 2/1978 | Naizer et al. | 73/23 |
| 4,170,455 | 10/1979 | Henrie | 23/232 R |
| 4,226,675 | 10/1980 | Lewis et al. | 176/19 R |
| 4,298,574 | 11/1981 | Bohl | 422/97 |
| 4,361,028 | 11/1982 | Kamiya et al. | 73/28 |
| 4,617,794 | 10/1986 | Fujitani et al. | 60/274 |
| 4,705,669 | 11/1987 | Tsuji et al. | 422/93 |
| 4,863,677 | 9/1989 | Eckardt | 376/313 |
| 4,911,890 | 3/1990 | Singh et al. | 422/62 |
| 5,017,331 | 5/1991 | Eckardt | 376/313 |
| 5,041,265 | 8/1991 | Koike et al. | 422/94 |
| 5,060,473 | 10/1991 | Nakagawa | 60/277 |
| 5,133,184 | 7/1992 | Geiger | 60/274 |
| 5,167,908 | 12/1992 | Chakraborty | 376/301 |
| 5,167,927 | 12/1992 | Karlson | 422/90 |
| 5,321,730 | 6/1994 | Eckardt | 376/301 |
| 5,374,400 | 12/1994 | Sprinkle et al. | 422/94 |

FOREIGN PATENT DOCUMENTS

| | | |
|---|---|---|
| 30 46 560 A1 | 7/1982 | Germany . |
| 34 38 659 | 4/1986 | Germany . |
| 3438569 | 4/1986 | Germany . |
| 40 40 734 A1 | 1/1992 | Germany . |
| 2153073 | 8/1985 | United Kingdom . |

*Primary Examiner*—Randy Gulakowski
*Assistant Examiner*—S. Carrillo
*Attorney, Agent, or Firm*—Herbert L. Lerner; Laurence A. Greenberg; Werner H. Stemer

[57] ABSTRACT

In order to determine a concentration of a gas mixture, especially a hydrogen concentration of a containment atmosphere of a nuclear power station, a temperature change resulting from a catalytic reaction is measured. The gas mixture is diluted with a motive gas of known composition. The dilution is carried out by a jet pump.

4 Claims, 2 Drawing Sheets

DEVICE DETERMINING A CONCENTRATION OF A GAS MIXTURE

CROSS-REFERENCE TO RELATED APPLICATION

This application is a Continuation-in-Part of U.S. application Ser. No. 08/367,707, filed Jan. 3, 1995, now abandoned, which is a Continuation of International Application Ser. No. PCT/DE93/00531, filed Jun. 21, 1993.

BACKGROUND OF THE INVENTION

FIELD OF THE INVENTION

The invention relates to a method for determining a fraction of a gas mixture in a containment atmosphere of a nuclear power station by measuring a temperature change resulting from a catalytic reaction. The invention further relates to a device for implementing the method.

It is known that hydrogen in the presence of a catalyst, for instance based on platinum or palladium, is oxidized in an exothermal reaction even at room temperature. That catalytic oxidation of hydrogen is also known as cold combustion. The hydrogen concentration in a gas mixture can be determined through the use of a measurement of the heat of reaction or temperature change resulting from the reaction.

Thus, for example, in a method disclosed by U.S. Pat. No. 4,298,574, the temperature change arising as a result of a catalytic oxidation of hydrogen on a catalyst is detected, with respect to a reference value, by means of a thermoelement, and is converted into a corresponding voltage signal. The measured voltage is a measure for the hydrogen fraction of the gas mixture. That method can also be used to determine the fraction of carbon monoxide or hydrocarbon in the gas mixture.

In a method disclosed by German Published, Non-Prosecuted Application DE 30 46 560 A1 for detecting flammable gases, especially hydrogen in the containment atmosphere of a nuclear power station, a temperature change is detected by means of a temperature-dependent ohmic resistor which forms part of a bridge circuit.

In order to ensure that a reactive hydrogen/oxygen mixture for the detection of hydrogen in an inert gas stream is obtained, a method disclosed by U.S. Pat. No. 4,072,043 involves the admixture of air to the inert gas (e.g. N2) prior to its entry into a detection chamber.

The known methods do pose the risk of the catalyst heating up as far as the ignition limit of an ignitable mixture. Due to the high heat release that may result in destruction of the catalyst. In the containment atmosphere of a nuclear power station, ignitable mixtures can react at high rates in an uncontrolled manner even with a hydrogen fraction of less than 10%, and reliable measurement of the fractions of the mixture are then no longer possible.

In order to enable satisfactory detection of a flammable gas, even if the concentration of the flammable gas in a gas sample increases beyond a limit value, Published UK Application GB 2 153 073 A, corresponding to U.S. Pat. No. 4,565,086, discloses pumping a diluent, especially ambient air, into a line carrying the gas sample.

SUMMARY OF THE INVENTION

It is accordingly an object of the invention to provide a method and a device for determining a fraction of a gas mixture, which overcome the hereinafore-mentioned disadvantages of the heretofore-known methods and devices of this general type, which provide a reliable method for determination of a fraction, especially a hydrogen and/or oxygen fraction, of a gas mixture in a containment atmosphere of a nuclear power station over a wide range and which provide a simple device for implementing the method.

With the foregoing and other objects in view there is provided, in accordance with the invention, a method for determining a fraction of a gas mixture in a containment atmosphere of a nuclear power station, which comprises diluting a gas mixture fed to a catalyst, with a motive gas of known composition, in a jet pump, for instance a Venturi nozzle or jet; and measuring a temperature change resulting from a catalytic reaction.

In accordance with another mode of the invention, the gas mixture is drawn in through a filter and is intimately mixed with the motive gas or a motive gas mixture through a nozzle, and the dilution is adjustable, preferably in the ratio of from 1:1 to 1:10, for example in the ratio of 1:4.

In accordance with a further mode of the invention, in order to determine the hydrogen or carbon monoxide fraction in the gas mixture, the motive gas contains an oxidizing fraction, preferably oxygen. The motive gas being used can then either be air or alternatively nitrogen, if sufficient oxygen is present in the gas mixture.

In accordance with an added mode of the invention, in order to determine the oxygen fraction in the gas mixture, the motive gas contains an oxidizable fraction, such as hydrogen or carbon monoxide.

With the objects of the invention in view, there is also provided a device for determining a fraction of a gas mixture in a containment atmosphere of a nuclear power station, comprising a catalyst; a motive gas line carrying a motive gas of known composition; a jet pump having an inlet side connected to the motive gas line and an outlet side connected to the catalyst, for diluting a gas mixture and moving the diluted gas mixture to the catalyst with the motive gas; and means for measuring a temperature change resulting from a catalytic reaction.

In accordance with another feature of the invention, the jet pump for diluting the gas mixture with the motive gas discharges the motive gas directly into the catalyst.

In accordance with a further feature of the invention, the jet pump is disposed, together with the catalyst, in a housing, with the option of a separate filter connected upstream of the pump.

Alternatively, in accordance with an added feature of the invention, the jet pump is connected to the catalyst through a line. In that case it is disposed in a separate housing which is at least partially gas-permeable and at the same time serves as a filter.

In both cases, the drive-nozzle of the jet pump is connected to a motive gas line which advantageously can be constructed in the form of a capillary line over at least part of its length.

In accordance with another feature of the invention, the jet pump is a single jet pump.

The advantages achieved by means of the invention are, in particular, that it is possible, by dilution of the gas mixture with a motive gas, to measure virtually as high a fraction of a mixture as one could wish. Thus, for instance in an analysis of the gas atmosphere of a containment enclosing the nuclear reactor in the case of massive hydrogen release, especially even with a substoichiometric oxygen fraction, hydrogen concentrations of more than 30% by volume can be observed, with the option of carrying out -the analysis both inside and outside the containment shell enclosing the containment atmosphere. This method can furthermore also be advantageously used for determining the fractions of a gas mixture flowing out from the primary circuit or other pressurized systems of a nuclear power station. In no case will the ignition temperature of a hydrogen-oxygen mixture be reached. Another advantage of the invention is the ability to both dilute and move the motive gas mixture to the catalyst utilizing a single jet pump. In addition, the ability to arrange all of the equipment within the containment shell of the nuclear power plant is another advantage of the invention.

It is possible to determine various fractions of a mixture by using different motive gases. In so doing, a calibration or switch-over between measuring ranges on one hand, e.g. between a first range for fractions up to 10% of a mixture and a second range for fractions of a mixture or concentrations above 10%, and changes in the motive gas composition for detecting different fractions of a mixture on the other hand, are possible within a short time.

Other features which are considered as characteristic for the invention are set forth in the appended claims.

Although the invention is illustrated and described herein as embodied in a method and a device for determining a fraction of a gas mixture, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
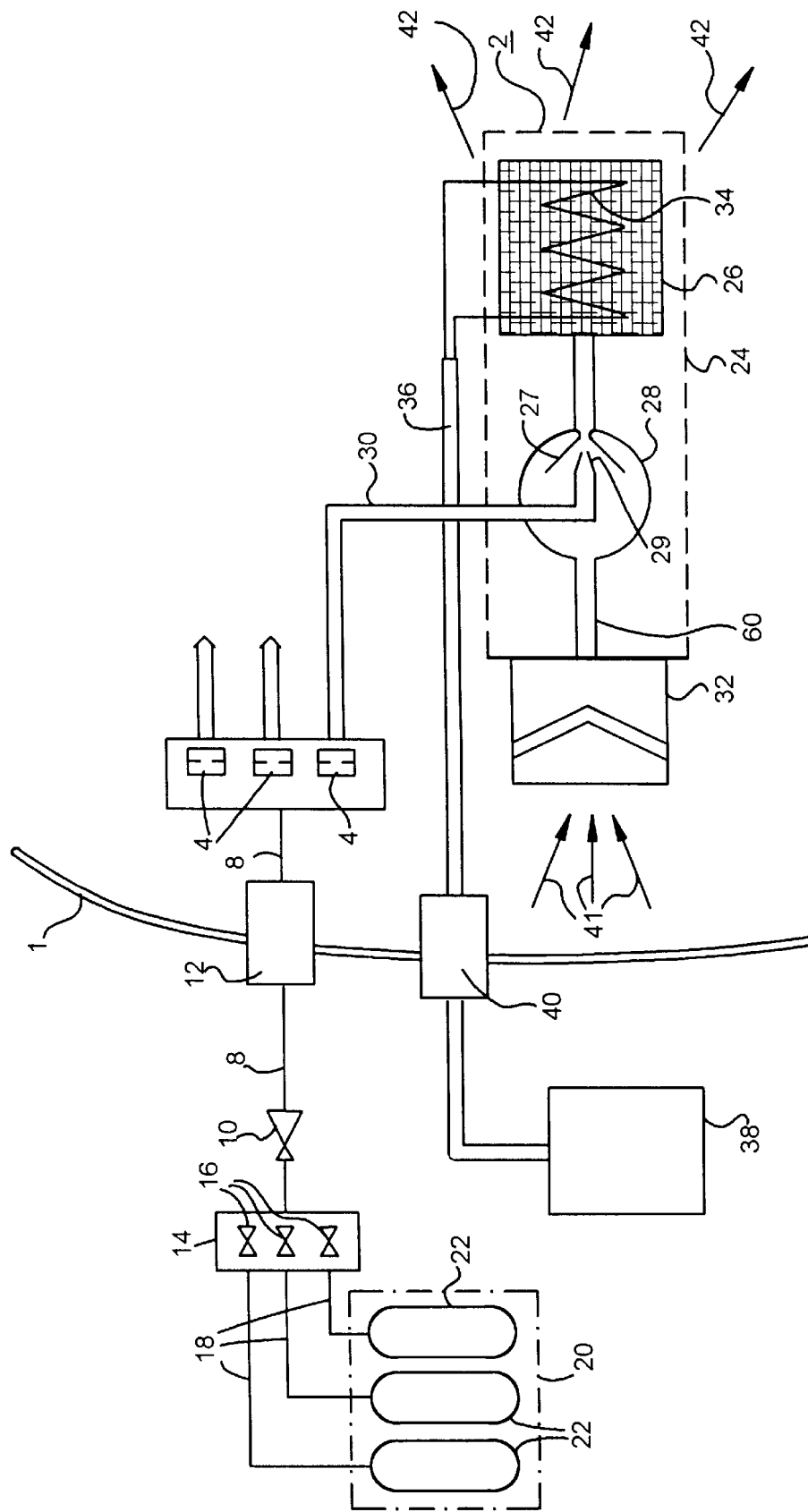
FIG. 1 is a fragmentary, diagrammatic, sectional view of a containment shell of a nuclear reactor with a schematic circuit diagram of a measuring device having a diagrammatically illustrated measuring head as an appliance for detecting fractions of a gas mixture.

Referring now in detail to the figures of the drawing, in which parts corresponding to one another are provided with the same reference symbols, and first, particularly, to FIG. 1 thereof, there is seen a measuring device which includes a number of measuring heads 2 that are disposed inside a containment shell 1, only one of which is depicted diagrammatically in FIG. 1. The illustrated measuring head 2, and all of the other measuring heads, are each connected through a respective restrictor 4 to a motive gas line 8. All of the restrictors are disposed in a common distributor box 6. The motive gas line 8, which incorporates a regulating unit or throttle valve 10, is connected through a duct or throughhole 12 in the containment shell 1, to a metering block 14 which has a number of valves 16. The metering block 14 is connected through gas lines 18 to a chamber 20 in which gas containers 22 installed. The gas containers 22 are each filled with a motive or calibration gas, for example with air, nitrogen, hydrogen or oxygen. The gas containers 22 and the metering block 14 may also be disposed inside the containment shell.

The measuring head 2 may, for example, be constructed in a manner similar to that of a diffusion measuring head disclosed by German Published, Non-Prosecuted Application DE 34 38 659 A1. The measuring head 2 includes a housing 24, in which a catalyst 26 and a jet pump 28, such as a Venturi jet or nozzle, are disposed. Instead of the jet pump 28 it is also possible to provide a different mixing device, for instance a static mixer. The housing 24 is formed wholly or in part of a sintered metal. Due to the porosity of the sintered metal it is gas-permeable, so that aerosols and moisture are retained.

The inlet side of the jet pump 28 is connected through a capillary line 30 to the distributor box 6 and discharges into the catalyst 26. In addition, the jet pump 28 communicates on the inlet side through a filter 32 with an interior space formed by the containment shell 1, i.e. with a containment atmosphere surrounding a non-illustrated nuclear reactor.

The catalyst 26 contains palladium or platinum as the catalytically active substance and has a net-like or waddinglike structure. Alternatively, however, the catalyst 26 may be wholly or partly of spiral construction in the form of a heatable filament. The catalyst 26 may be supplied through the motive gas line 8 with a regenerating gas. As a result, regeneration of the catalyst material is possible even at temperatures above 500° C.

In order to determine temperature changes in the vicinity of the catalyst 26, a temperature sensor 34 is provided which is connected through an instrument lead 36 to a device 38 for processing the measured values, e.g. in a control room. The instrument lead 36 is run through a duct or bushing 40 in the containment shell 1. A temperature-dependent electrical resistor assigned to a bridge circuit is particularly suitable as the temperature sensor 34. However, the same purpose may also be served by a thermoelement or a coil having a temperature-dependent inductance.

The containment atmosphere enclosed in the containment shell 1 is a gas mixture which, under certain operating conditions, contains hydrogen, carbon monoxide, oxygen and/or hydrocarbon as fractions of the mixture. In order to determine a fraction of the mixture, the motive gas is supplied from one of the containers 22 through the motive gas line 8 and through the capillary line 30 to the jet pump 28. The motive gas flow rate is adjusted by means of the regulating unit 10. The adjustment expediently takes place automatically as a function of the pressure or of the temperature of the gas mixture and as a function of the concentration of a fraction of the gas mixture, and especially as a function of the hydrogen concentration. The regulating unit 10 effects largely constant-volume throttling of the motive gas flow rate. In the process, the motive gas reaches Laval velocity, for a pressure ratio of ½ between the gas mixture pressure within the containment shell 1 and the motive gas pressure. Distribution of the motive gas over the individual measuring heads 2 takes place in the distributor box 6.

The gas mixture flowing through the filter 32 into a gas mixture line 60 and then into the jet pump 28 in the direction of arrows 41 is mixed in a mixing nozzle 27 of the jet pump 28 with a motive gas jet escaping at high velocity from a drive nozzle 29 of the jet pump 28. In the process, if the drive pressure of the gas mixture to be measured is sufficiently high, e.g. due to a pressure increase within the containment shell 1, the motive gas can be drawn in by the gas mixture. The gas mixture that is thus diluted with the motive gas, which has a composition that is known, flows to the catalyst 26 and escapes from the measuring head 2 in the direction of arrows 42. Therefore, both the dilution and the movement of the gas can be accomplished by a single jet pump or by a combination of jet pumps. The dilution is adjusted in the regulating unit 10 and/or in the distributor box 6, with the ratio being, for example, 1:4.

The catalytic oxidation takes place at the catalyst 26 and the heat of reaction or temperature change is detected by means of the temperature sensor 34. In other words, the detected temperature change results from the catalytic reaction taking place at the catalyst 26. The temperature change is converted into a corresponding voltage signal. Based on the level of the voltage signal or a change with respect to a reference signal, while taking the dilution ratio into account, the device 38 determines the fraction of the mixture, e.g. the hydrogen or oxygen concentration in the containment atmosphere.

The motive gas which is used for determining the hydrogen concentration is nitrogen, or it is air or oxygen-enriched air if not enough oxygen is present in the containment atmosphere. In order to determine the oxygen fraction, if only small amounts of hydrogen have been released, the motive gas is admixed with carbon monoxide or hydrogen as the oxidizable fraction.

Figure 2:
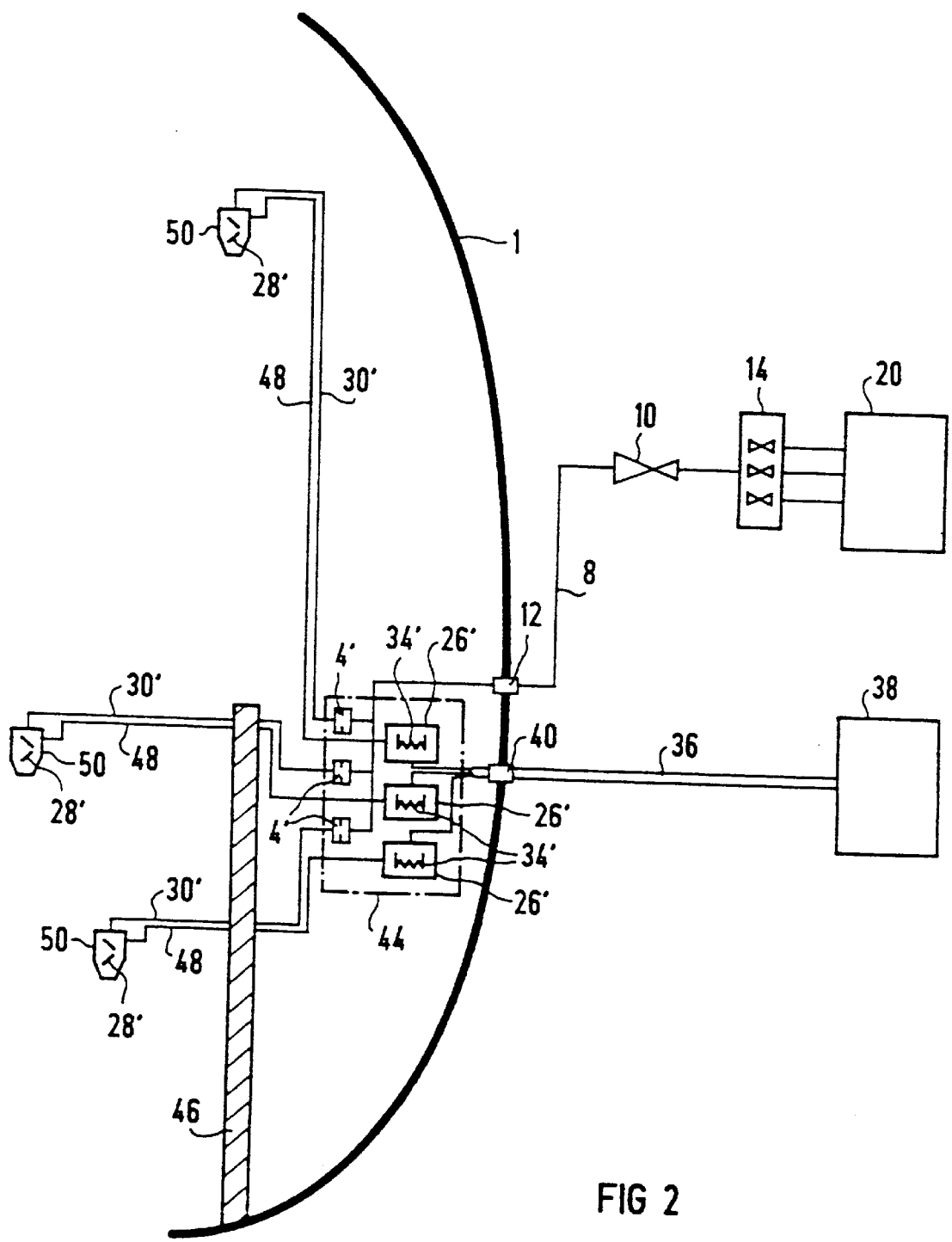
FIG. 2 is a view similar to FIG. 1 showing a measuring device having a number of dilution appliances disposed in a distributed manner and catalysts disposed in a common measuring box.

In the measuring device shown in FIG. 2, a plurality of catalysts 26' are combined in a central measuring box 44, which is protected, for instance against flying debris inside the containment shell 1, by a wall 46. Dilution devices or jet pumps 28', which connected to the measuring box 44 through respective inflow and outflow lines 30' and 48, are disposed in a distributed manner within the containment shell 1. The jet pumps 28', which are only diagrammatically shown in FIG. 2, are each surrounded by a housing 50 that at the same time serves as a filter. Each housing 50 is at least partially formed of a gas-permeable material, e.g. of a sintered metal or a metal fiber mesh. This prevents liquid components or coarse contaminants from reaching the jet pumps 28' together with the gas mixture.

The motive gas which is passed through the motive gas line 8 is fed through the inflow lines 30' to the jet pumps 28'. Restrictors 4', which are situated in the inflow lines 30' and are disposed within the measuring box 44, again serve to distribute the motive gas over the individual jet pumps 28'.

The gas mixture reaches the respective jet pumps 28' through the housings 50 serving as filters and is mixed with the motive gas flowing through the inflow lines 30'. In the process, the gas mixture is dried at the same time, so that condensation of residual humidity contained in the gas mixture, e.g. in cool regions of the space within the containment shell 1, is reliably avoided. The gas mixture which is thus diluted reaches the respective catalyst 26' through the outflow lines 48. The temperature change of each catalyst 26' is measured separately by means of a temperature sensor 34'. Corresponding output signals are passed through the lead 36 to the device 38 for processing the measured values.

In the embodiment according to FIG. 2, the fault-proneness of the assemblies or measuring modules, which are disposed in a distributed manner within the containment shell 1 and each of which only include a jet pump 28', is particularly low.

What is claimed is:

1. A device for determining a concentration of a gas mixture in a containment atmosphere of a nuclear power station, comprising:

a catalyst;

a motive gas line carrying a motive gas of known composition;

a jet pump having a first inlet communicating with said motive gas line and a second inlet separate from said first inlet for receiving a gas mixture from a containment atmosphere, said jet pump forming a diluted gas mixture by admixing the motive gas to the gas mixture, and said jet pump having an outlet connected to said catalyst for moving the diluted gas mixture to said catalyst; and a temperature sensor disposed in said catalyst, said temperature sensor measuring a temperature change resulting from a catalytic reaction of the diluted gas mixture with said catalyst and producing a signal indicative of the concentration of the gas mixture.

2. The device according to claim 1, including a filter for filtering the gas mixture and for supplying the gas mixture to said second inlet of said jet pump, said filter for filtering the gas mixture and for supplying the gas mixture to said second inlet of said jet pump, said filter being connected upstream of said jet pump.

3. The device according to claim 1, including a gas-permeable housing in which said jet pump is disposed, and an outflow line connecting said jet pump to said catalyst.

4. The device according to claim 1, wherein said jet pump is a single jet pump.

* * * * *